United States Patent [19]

Dalmasso et al.

[11] Patent Number: 5,770,393
[45] Date of Patent: Jun. 23, 1998

[54] BIOLOGICAL INDICATOR FOR DETECTION OF EARLY METABOLIC ACTIVITY

[75] Inventors: Joseph P. Dalmasso, Apex; David A. Freeman, Raleigh, both of N.C.

[73] Assignee: Steris Corporation, Mentor, Ohio

[21] Appl. No.: 831,318

[22] Filed: Apr. 1, 1997

[51] Int. Cl.[6] .............................. C12Q 1/22; C12Q 1/40; C12N 3/00; C12N 1/00
[52] U.S. Cl. ............................ 435/31; 435/22; 435/242; 435/252.31; 435/252.1; 435/252.5; 435/832; 435/835; 435/839; 435/968; 435/963; 534/653
[58] Field of Search ................................ 435/31, 252.31, 435/252.1, 252.5, 832, 835, 839, 968, 22, 963, 242; 534/653

[56] References Cited

U.S. PATENT DOCUMENTS

| | | | |
|---|---|---|---|
| 3,846,242 | 11/1974 | Ernst | 435/31 |
| 4,087,326 | 5/1978 | Kereluk | 195/103.5 R |
| 4,461,837 | 7/1984 | Karle et al. | 435/296 |
| 4,717,661 | 1/1988 | McCormick et al. | 435/31 |
| 4,914,034 | 4/1990 | Welsh et al. | 435/296 |
| 4,958,016 | 9/1990 | Kerkenaar et al. | 536/123 |
| 5,030,832 | 7/1991 | Williams et al. | 250/458.1 |
| 5,063,297 | 11/1991 | Hardenbrook et al. | 250/458.1 |
| 5,073,488 | 12/1991 | Matner et al. | 435/31 |
| 5,223,401 | 6/1993 | Foltz et al. | 435/18 |
| 5,334,841 | 8/1994 | Grassle et al. | 250/458.1 |
| 5,366,872 | 11/1994 | Hird et al. | 435/31 |
| 5,418,167 | 5/1995 | Matner et al. | 435/288 |
| 5,486,459 | 1/1996 | Burnham et al. | 435/31 |

FOREIGN PATENT DOCUMENTS

WO 95/21936 8/1995 WIPO .

OTHER PUBLICATIONS

"Culture Conditions for Production of Termostable Amylase by *Bacillus stearothermophilis*", Srivastava, et al., Applied and Environmental Microbiology, Jul. 1986, pp. 179–184.

"The Extracellular α–Amylase of *Bacillus stearothermophilus*", Pfueller, et al. The Jour. of Biol,ogical Chemistry, V. 244, No. 1, Jan. 10, 1969, pp. 48–54.

"The Preparation of Enzymes by Fermentation", Nyiri, International Chemical Engineering, vol. 11, No. 3, Jul. 1971, pp. 447–457.

"Hybrid α–Amylases Produced by Transformants of *Bacillus subtilis*", Part II Biochimica et Biophysica Acta 365 (1974) 248–358.

"Hybrid α–Amylases Produced by Transformants of *Bacillus subtilis*", Part I Biochimica et Biophysica Acta 365 (1974) 235–347.

"Extracellular Enzyme Synthesis in the Genus Bacillus", Priest, Bacteriological Reviews, Sep. 1977, pp. 711–753.

"A New Method for the Determination of α–Amylase", Experentia 23, 705, (1967).

*Primary Examiner*—Louise Leary
*Attorney, Agent, or Firm*—Fay, Sharpe, Beall, Fagan, Minnich & McKee

[57] ABSTRACT

A bacteria impermeable container or ampule (10) contains a liquid growth medium and a substrate-indicator complex. The complex includes a substrate component, e.g., starch, and an indicator molecule, e.g., a dye, a fluorescent molecule, or the like, which are tightly bound and complexed, but which are cleavable by a preselected enzyme. A sterilant passes over a carrier (20) for microorganisms which, upon germination, are capable of rapidly generating large quantities of the preselected enzyme. Following the sterilization process, the carrier is immersed in the liquid growth medium. Any viable surviving microorganisms grow, generating the preselected enzyme. The enzymes cleave the bound indicator molecule from the substrate, resulting in a measurable property change in a couple of hours. Typical property changes include fluorescence, a color change, a change in pH which triggers a pH indicator color change, and the like.

25 Claims, 2 Drawing Sheets

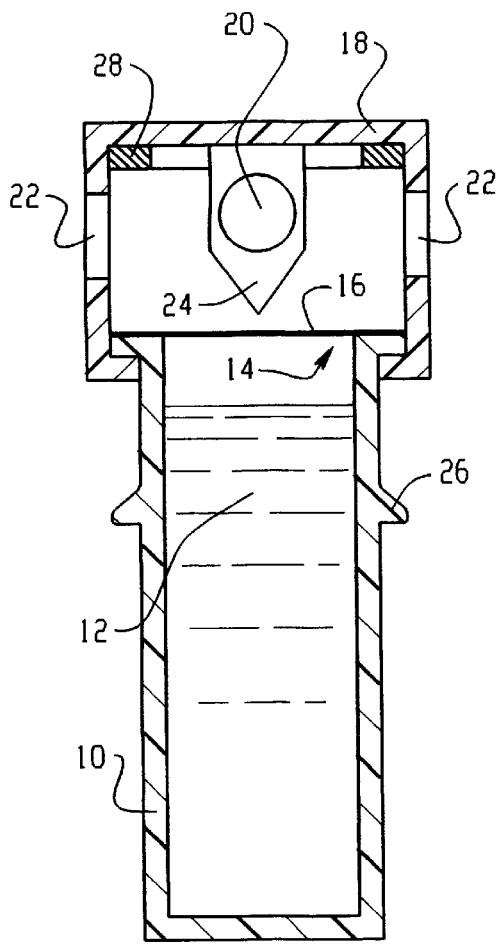
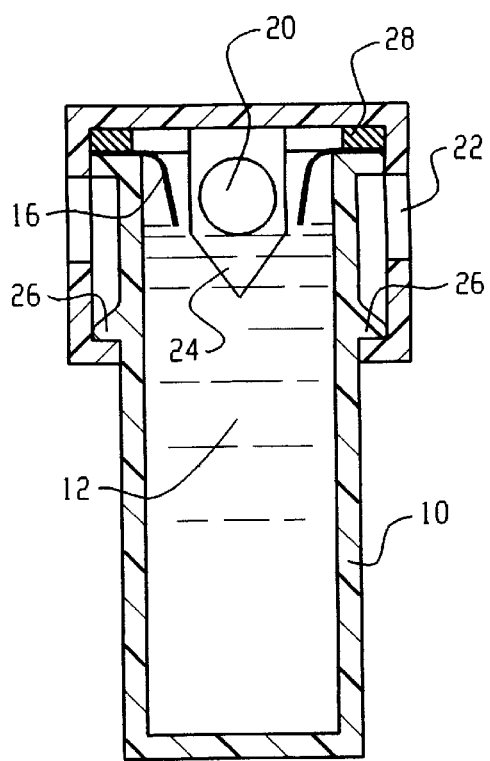
Fig. 1
Fig. 2
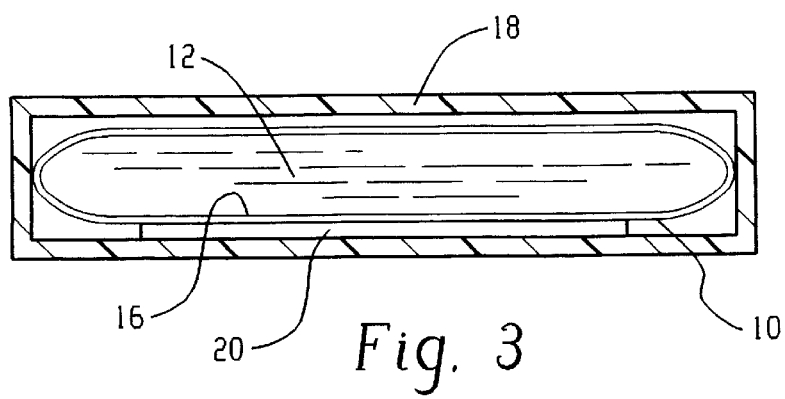
Fig. 3

BIOLOGICAL INDICATOR FOR DETECTION OF EARLY METABOLIC ACTIVITY

BACKGROUND OF THE INVENTION

The present invention relates to the sterilization assurance arts. It finds particular application in conjunction with biological indicators using microorganisms for determining the effectiveness of sterilization processes and will be described with particular reference thereto. It should be appreciated, however, that the invention is also applicable to assessing the resistance of microorganisms to other physical and chemical treatments.

Currently, the method of choice for monitoring the effectiveness of a sterilization cycle is the biological indicator. A typical biological indicator contains a calibrated population of bacterial spores having a high resistance to the sterilization process under investigation. After exposure to the sterilization cycle, the indicator is incubated in a bacteriological nutrient media to encourage outgrowth of any remaining viable spores. Subsequent bacterial growth is an indication that the sterilization process was ineffective.

Bacterial spores are utilized as biological indicator organisms because they are highly resistant to the physical and chemical agents utilized in the sterilization process and because their biological stability permits the manufacture of a product that exhibits a long shelf life relative to one comprising vegetative cells. The choice of bacteria is dependent on the sterilization process employed. For example, *Bacillus stearothermophilus* spores are used to monitor moist heat sterilization and hydrogen peroxide sterilization because of their high resistance to these processes. Similarly, *Bacillus subtilis* spores are employed to monitor ethylene oxide sterilization, dry heat sterilization, and sterilization systems utilizing peroxy compounds in the plasma state.

Commercially used biological indicators have frequently required incubation periods in excess of forty-eight hours for a detectable level of spore outgrowth to be obtained. In hospitals, quarantine of processed loads for such a period of time is not pragmatic due to the high cost of having medical devices inactive. Therefore, the shorter the incubation period, the faster the processed loads can be returned to use with complete confidence in their sterility.

The need for a sterility indicator capable of providing a more rapid indicator of sterilization efficiency has led to consideration of the use of thermostable enzymes in place of microorganisms. For example, U.S. Pat. Nos. 5,073,488 and 5,418,167, both of Matner describe devices by which the activity of microbial enzymes after sterilization may be correlated with spore viability, thereby giving an indication of the efficiency of sterilization.

Although thermostable enzymes provide a valuable tool for determining the effectiveness of a sterilization process, they do not give the same degree of sterilization assurance as biological indicators. Because the activity of a thermostable enzyme can only be correlated with spore death, the degree of inactivation of such an enzyme may not accurately measure the effect of the sterilization process on living organisms in all instances.

The present invention provides a new and improved biological indicator for accurately determining the effectiveness of a sterilization cycle.

SUMMARY OF THE INVENTION

In accordance with one aspect of the present invention, a self-contained biological indicator is provided for determining the effectiveness of a sterilization process. A bacteria impermeable container contains a liquid growth medium and has a bacteria impermeable, frangible barrier portion. A carrier supports microorganisms which exhibit a high resistance to the sterilization process. The carrier is disposed within a cover member. The cover member is movable between a first position in which the carrier is separated from the liquid growth medium by the barrier and a second position in which the barrier portion is broken and the carrier becomes immersed in the liquid growth medium. This permits the liquid growth medium to provide nutrients for the growth of said microorganisms as remain viable after the sterilization process. Any remaining viable microorganisms commence the generation of enzymes. A detection system specific for the enzymes includes a combined substrate and indicator. The combined substrate and indicator are cleaved by the enzyme into the substrate and the indicator, resulting in a measurable change in at least one property of the indicator.

In accordance with another aspect of the present invention, a biological indicator is provided for measuring the metabolic activity of indicator organisms that survive an inadequate sterilization cycle. Spores are located on or impregnated in a carrier material. A liquid growth media is contained separately in a sealed ampule. At a time after exposure to the sterilization cycle, the ampule is broken open and the spore carrier immersed in the liquid growth medium to provide nutrients for the outgrowth of spores not killed in the sterilization cycle. The outgrowth of any spores not killed generates an enzyme. A substrate-indicator complex is disposed in the growth medium and is cleaved by the enzyme generated by the spore outgrowth into a substrate component and an indicator molecule. The indicator molecule causes a change in an optically measurable property of the growth medium.

In accordance with another aspect of the present invention, a method is provided for assessing the efficiency of sterilization. Microorganisms which exhibit a high sterilization resistance and which generate a selected enzyme during growth are subject to a sterilization process. After the sterilization process, the microorganisms, a detection complex which is cleaved into separate substrate and indicator components by the selected enzyme, and a liquid growth medium are brought together. The microorganisms, the detection complex, and the growth medium are incubated under conditions sufficient to promote the growth of the microorganisms, the generation of the selected enzymes, and the cleaving of the detection complex by the enzymes. Changes attributable to the cleaved indicator component are detected.

One advantage of the present invention is that it reduces the time required to obtain an accurate assessment of the effectiveness of a sterilization process, allowing sterilized items to be returned to use in confidence.

Another advantage of the present invention is that the indicator does not rely on a correlation of inactivation of an enzyme with spore death, but rather measures the effects of the sterilization process on the microorganisms themselves, giving greater assurance that the sterilization process was adequate.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 1 is a cross sectional view of a biological indicator in accordance with the present invention;

FIG. 2 is a cross sectional view of a biological indicator in accordance with the present invention with its cover in the closed position;

FIG. 3 is a cross sectional view of an alternative embodiment of a biological indicator in accordance with the present invention; and, FIG. 4 is a diagrammatic illustration of an example of a reader for the biological indicators of FIGS. 1, 2 or 3.

DETAILED DESCRIPTION OF THE PREFERRED EMBODIMENTS

Figure 4:
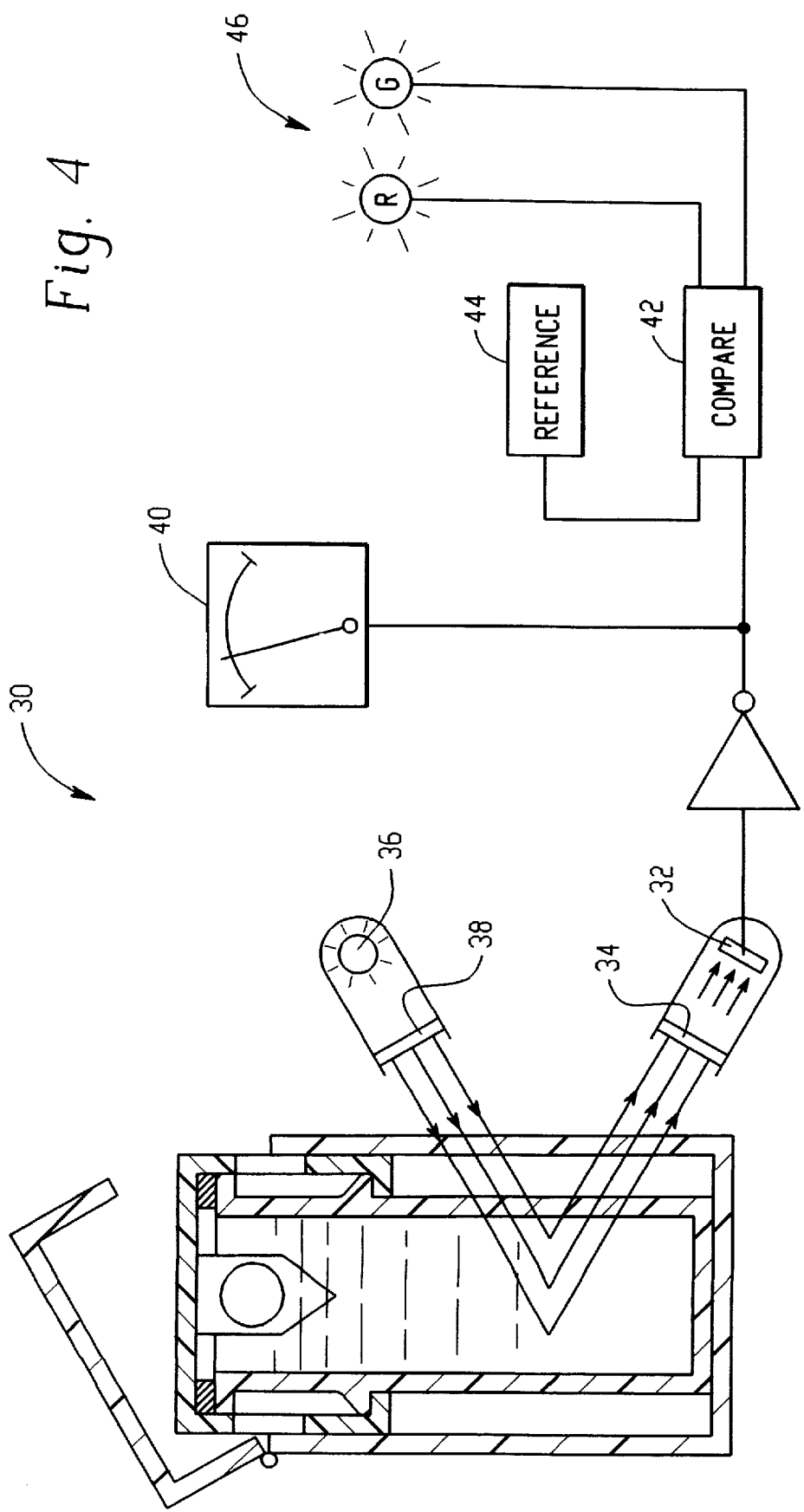

With reference to FIGS. 1 and 2, a preferred embodiment of the biological indicator of the present invention is shown. A bacteria impermeable container 10 is made from a material which will withstand the temperature and chemicals employed in the sterilization process. The preferred shape of the container is a cylindrical tube, although other container shapes are also contemplated. The container holds a liquid growth medium 12 and has an access opening 14. A bacteria impermeable barrier 16 covers the access opening 14 during a sterilization process. The barrier is preferably constructed from a material which does not rupture under the sterilization conditions, thereby preventing loss of the liquid growth medium during sterilization. A cover, or cap, 18 is mounted on the container.

A carrier 20, which supports microorganisms, is preferably constructed of soft paper, although other materials which are resistant to the sterilization process and which do not inhibit microorganism growth are also contemplated. Microorganisms which exhibit a high resistance to the sterilization cycle, are disposed on the carrier, preferably in such a way that they are not physically removed during the sterilization process. Preferably the carrier is mounted within the cap, although it is also contemplated that the microorganism may be carried on the inner surfaces of the cap or on the barrier.

During the sterilization process the cap is positioned away from the barrier, with apertures 22 open, to allow a sterilant, for example steam or ethylene oxide, to pass over the carrier 20 and act upon the microorganisms. On completion of the sterilization process, the cap is moved toward the container to a second, or closed position. In one preferred embodiment, a dart 24 or other cutting edge penetrates the impermeable barrier 16 and immerses the microorganism carrier 20 in the liquid growth medium 12. The movement of the cap to the closed position causes detents 26 to engage the cap 18 holding a seal 28 against the container 10. In this manner, the microorganisms are brought into contact with the growth medium simultaneously with sealing the biological indicator, thereby preventing additional microorganisms from entering the system.

With reference to FIG. 3, in another preferred embodiment, the cover 18 surrounds the container 10. Flexing or movement of the cover from the first to the second position ruptures the container thereby immersing the carrier 20 in the growth medium 12. In this embodiment, the barrier 16 includes a frangible area of the container wall.

The liquid growth medium 12 provides nutrients for the growth of any microorganisms that remain viable after the sterilization process and for the generation of enzymes by the microorganisms. A growth medium is selected which does not significantly degrade during the sterilization process and does not interfere with detection of the enzymes produced by the growing microorganisms.

A detection system 30 is specific for at least one enzyme produced by the growing microorganisms. A combined substrate and indicator, or substrate-indicator complex, is the basis of the detection system and is cleaved into substrate and indicator components by the generated enzymes, resulting in a measurable change in a property or properties of the indicator. The microorganisms, combined substrate and indicator, and growth medium are incubated together, under conditions favorable to the generation of enzymes by any remaining viable microorganisms and to the cleaving of the complex by the enzymes.

Preferred methods for detecting the change in a property of the indicator include fluorometric, visual, pH, and spectroscopic methods. The detection of a measurable change in an indicator property within an established period of time indicates growth of the microorganisms, hence inadequate sterilization. The absence of a measurable change within the established period of time demonstrates that the sterilization process was lethal to the test microorganism and therefore adequate.

With reference to FIG. 4, in one preferred embodiment, the indicator is a fluorescent dye and the detection system 30 includes light, a photodetector 32 for detecting light of a selected wavelength, corresponding to the wavelength at which the substrate-indicator complex or the indicator component fluoresces. A filter 34 can be utilized to restrict the spectrum of the collected light. Where appropriate, a light source 36 of a wavelength for stimulating luminescence in the indicator is provided. A filter 38 assures that light of the wavelength emitted by the indicator is blocked from being reflected to the detector 32. A quantitative read out 40 indicates the amount of light emitted by the indicator. An analyzer 42 compares the detected light with that of a reference 44. A qualitative readout 46 indicates whether or not the sterilization process was effective.

It is also contemplated that the biological indicator may be used in the conventional manner, wherein the outgrowth of spores over a period of approximately forty-eight hours or less is detected visually, as an additional check on sterilization efficiency.

Suitable microorganisms include bacteria and fungi, with a spore producing bacteria being preferred. In addition to exhibiting a high resistance to the sterilization process, the selected microorganism secretes a sufficient quantity of the enzyme to be detected by the detection system within a selected incubation time. Particularly preferred microorganisms include *Bacillus stearothermophilus, Bacillus subtilis*, and *Bacillus circulans*.

The present invention, although described primarily in terms of a single microorganism species, should be understood to refer as well to a plurality of microorganism species. For example, a biological indicator may contain a number of microorganisms, each of which is particularly resistant to a different method of sterilization.

The enzyme is preferably one which is extracellular and is not present in appreciable quantities in non-viable microorganisms. A particularly preferred enzyme is alpha amylase which is secreted in sufficient quantities by certain microorganisms, in particular, the spore producing bacterium *Bacillus subtilis*, to allow early detection of microbial activity. When the enzyme whose activity is to be detected is alpha amylase, the substrate in the detection system is preferably a starch. Other preferred enzymes includes proteases.

The substrate-indicator complex is preferably dispersed within the container 10, dispersed through the culture medium, such that the enzymes generated by the microorganism do not commence acting upon the complex until the sterilization process is complete. It is contemplated, however, that the complex can be disposed within the cover, on the inner surfaces of the cover, on the dart 24, on a carrier layered over or under barrier 16, on the microorganism carrier, interspersed with the microorganisms, or the like.

Where the substrate-indicator complex is disposed within the growth medium 12, the reaction of the enzymes with the complex following the penetration of the barrier by the microorganism carrier commences immediately on the growth of any surviving viable microorganisms. The complex is stable at the sterilization and incubation temperatures and resistant to the growth medium. Where the substrate-indicator complex is disposed within the cover, the complex is also stable under the sterilization conditions.

Preferably, the detection system is one which detects a change in a property of the indicator within eight hours or less and most preferably within two or less hours. When the enzyme to be detected is an amylase, the preferred substrate is an amylose starch and the preferred indicators are biologically active molecules, fluorescent dyes, dyes, chromogenic substances, pigments, acids, bases, and radio-labelled compounds. In one preferred embodiment, the selected indicator is an Azure Blue Dye. The combined substrate and indicator complex in this embodiment is preferably insoluble, with the complex suspended in the growth medium. The action of the enzymes upon the complex cleaves the bond between the dye and the starch releasing the soluble Azure Blue dye into the liquid growth medium. The color change in the growth medium is detected visibly or spectroscopically. One preferred indicator complex is product #57629 Starch Azure Potato Starch of Sigma Chemical Co. of St. Louis, Mo. Other examples of biologically active molecules include antibodies and enzymes.

A number of chromogenic substances have proved useful in enzymological procedures, including 5-bromo-4chloro-3-indolyl derivatives; indoxyl derivatives, nitrophenyl derivatives, and phenolphtalein derivatives. Another example of dyes include Remazol Brillant Blue which can be bonded to insoluble potato starch with covalent bridges to form Starch Azure. A concentration of Starch Azure in the range of 0.25-2% as a suspension when incubated at 60°C. with five spores of *Bacillus stereothermophilus* in a growth medium of 30% TSB, 1% dextrin, 0.1% $CaCl_2$ and 0-35 soluble starch yielded a detectable color change within four hours.

Another preferred class of indicators are molecules which exhibit fluorescence when cleaved from the combined substrate and indicator complex, as well as molecules which cease to fluoresce when cleaved. The prior art includes a number of fluorogenic substances for use in enzymatic procedures, many of which are commercially obtainable. (M. Roth, Methods of Biochemical Analysis, Vol. 17, D. Block, Ed., Interscience Publishers, N.Y., 1969, p. 189; S. Udenfriend, Fluorescence Assay in Biology and Medicine, Academic Press, N.Y., 1962, p. 312; and D. J. R. Lawrence, "Fluorescence Techniques for the Enzymologist", Methods in Enzymology, Vol. 4, S. P. Colowick and N. O. Kaplan, Eds., Academic Press, N.Y., p. 174, incorporated herein by reference). When the enzyme whose activity to be detected is an amylase, a particularly preferred substrate-fluorescent indicator complex embodiment is a casein-fluorescein conjugate c2990 (as supplied by Molecular Probes, Eugene, Oregon). Other preferred fluorogens for the detection of amylase include p-nitrophenol and 7-amino-4-methyl coumarin. other preferred indicators include those in which the indicator is a fluorescent molecule which modifies the fluorescence of a second fluorescent molecule. For example, the fluorescent substrate-indicator complex fluoresces with a first characteristic wavelength and the indicator alone fluoresces with a second characteristic wavelength. A fluorometer determines the presence of the indicator from a change in the fluorescence spectrum.

The preferred concentration of the combined substrate and indicator complex is dependant on the choice of substrate and enzyme, the method of detection selected, and the desired detection period. Preferably, the amount of the complex is sufficient to yield detectable quantities of the indicator component, in the presence of the enzyme, within a period of two hours following the completion of the sterilization process.

The types of growth media usefully employed in the present invention are widely known in the art. Examples of preferred growth media are aqueous solutions of soybean-casein digest broth, Dextrose Tryptone, and fluid thioglycollate. A particularly preferred growth medium in all of the above examples is Trypticase Soy Broth. Other liquid growth media which are compatible with the detection system and are not a competitive inhibitors for the enzyme are also suitable.

Preferably, the growth medium also contains a substance which reduces the toxicity of the growth medium toward the enzyme. A particularly preferred toxicity reducing substance is activated charcoal. Another is bouine serum albumin. Where the selected enzyme is an amylase, a particularly preferred toxicity reducing substance is a soluble starch, such as amylodextrin or amylogen, which also aids in the recovery of injured microorganisms. The concentration of the starch should not so high that it interferes with the reaction of the amylase and the combined substrate and indicator complex. A concentration of 0.35 wt.%- soluble starch is sufficient to aid recovery of injured microorganisms without appreciably interfering with the amylase reaction.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A self-contained biological indicator for determining the effectiveness of a sterilization process, the biological indicator comprising:

(a) a bacteria impermeable container containing a liquid growth medium and including a bacteria impermeable frangible barrier portion;

(b) a carrier which supports microorganisms exhibiting a high resistance to said sterilization process;

(c) a cover member within which the carrier is disposed, the cover member being moveable between a first position in which the carrier is separated from the liquid growth medium, the barrier portion, and a second position in which the barrier portion is broken and the carrier becomes immersed in the liquid growth medium, permitting said liquid growth medium to provide nutrients for the growth of said microorganisms remaining viable after the sterilization process and for the generation of enzymes by said viable microorganisms;

(d) a detection system, specific for said enzymes, including a combined substrate and indicator which are modified and/or cleaved by said enzyme into the substrate and the indicator, resulting in a measurable change in at least one property of said indicator.

2. The biological indicator of claim 1, wherein said microorganisms includes spore producing bacteria.

3. The spore producing bacteria of claim 2, wherein said spore producing bacteria is an enzyme secreting bacteria and is one of the group consisting of *Bacillus stearothermophilus*, *Bacillus subtilis*, and *Bacillus circulans*.

4. The biological indicator of claim 1, wherein said substrate includes a biological molecule selected from the group consisting of carbohydrates and proteins.

5. The biological indicator of claim 1, wherein said enzyme is secreted from said viable microorganisms during growth.

6. The biological indicator of claim 1, wherein said enzyme includes an alpha amylase and wherein said substrate includes a starch.

7. The biological indicator of claim 1, wherein the cover member surrounds essentially all the container and wherein the movement of the cover member from the open to the closed position ruptures the container, thereby immersing the carrier in the growth medium.

8. The biological indicator of claim 1, wherein said combined substrate and indicator are disposed in said growth medium such that a reaction of said detection system with said enzymes occurs upon the carrier penetrating said container.

9. The biological indicator of claim 1, wherein said indicator of said detection system is selected from the group consisting of biologically active molecules, fluorescent dyes, dyes, pigments, and radio-labelled compounds.

10. The biological indicator of claim 1, wherein said combined substrate and indicator is insoluble and wherein said indicator includes an Azure Blue dye which is visibly or spectroscopically detectable.

11. The biological indicator of claim 1, wherein said indicator includes a biologically active molecule which reacts with antigens or reagents to produce a detectable product.

12. The biological indicator of claim 1, wherein said indicator is a molecule which exhibits fluorescence when cleaved from said combined substrate and indicator.

13. The biological indicator of claim 12, wherein said molecule which exhibits fluorescence includes a fluorescence conjugate and wherein said substrate includes casein.

14. The biological indicator of claim 1, wherein said indicator is a fluorescent molecule which modifies the fluorescence of a second fluorescent molecule.

15. The biological indicator of claim 1 wherein the detection system includes an emission source of light, a detector for detecting light of a selected wavelength, an analyzer for comparing the detected light with a reference and a readout for indicating the effectiveness of the sterilization process.

16. The biological indicator of claim 1, wherein said indicator includes a pigment.

17. The biological indicator of claim 1, wherein said growth medium contains a substance which reduces the toxicity of said growth medium toward said enzyme.

18. The biological indicator of claim 17, wherein the toxicity reducing substance includes activated charcoal.

19. The biological indicator of claim 17, wherein said toxicity reducing substance includes a soluble starch and wherein said enzyme is an amylase.

20. The biological indicator of claim 1, wherein said enzyme is an amylase, and wherein said indicator in said detection system is a fluorescent molecule and wherein detection of said viable microorganisms is achieved in under 2 hours.

21. A self-contained biological indicator for measuring the metabolic activity of indicator organisms that survive an inadequate sterilization cycle including a spore carrier material with spores located on or impregnated in the carrier material, a liquid growth media which is contained separately in a sealed ampule, at a time after exposure to the sterilization cycle, the ampule being broken open and the spore carrier immersed in the liquid growth medium to provide nutrients for the outgrowth of spores not killed in the sterilization cycle, the outgrowth of any spores not killed generating an enzyme, further comprising:

a substrate-indicator complex which is dispersed in the growth medium and which is cleaved by the enzyme generated by the spore outgrowth into a substrate component and an indicator molecule which changes in an optically measurable property of the growth medium.

22. A method for assessing the efficiency of sterilization comprising:

(a) subjecting microorganisms, which exhibit a high sterilization resistance and which generate a preselected enzyme during growth, to a sterilization process;

(b) after the sterilization process, bringing together the microorganisms, a detection complex which is cleaved into substrate components and indicator components by said preselected enzyme, and a liquid growth medium;

(c) incubating the microorganisms, the detection complex, and the growth medium under conditions sufficient to promote the growth of microorganisms, generation of the preselected enzyme, and cleaving of the detection complex by the enzymes;

(d) detecting changes attributable to said cleaved indicator component.

23. The method as set forth in claim 22 wherein the substrate component is selected from the group consisting of carbohydrates and proteins.

24. The method as set forth in claim 22 wherein the indicator component is selected from the group consisting of biologically active molecules, fluorescent dyes, dyes, pigments, and radio-labelled compounds.

25. The method set forth in claim 22 wherein the enzyme includes alpha amylase.

* * * * *